United States Patent
Kobayashi et al.

(10) Patent No.: US 11,071,444 B2
(45) Date of Patent: Jul. 27, 2021

(54) MEDICAL ENDOSCOPE SYSTEM PROVIDING ENHANCED ILLUMINATION

(71) Applicant: Sony Olympus Medical Solutions Inc., Tokyo (JP)

(72) Inventors: Motoaki Kobayashi, Tokyo (JP); Sumihiro Uchimura, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 618 days.

(21) Appl. No.: 15/877,161

(22) Filed: Jan. 22, 2018

(65) Prior Publication Data

US 2018/0256018 A1    Sep. 13, 2018

(30) Foreign Application Priority Data

Mar. 9, 2017  (JP) ............................... JP2017-45354

(51) Int. Cl.
*A61B 1/06* (2006.01)
*A61B 1/012* (2006.01)
(Continued)

(52) U.S. Cl.
CPC ............ *A61B 1/0661* (2013.01); *A61B 1/002* (2013.01); *A61B 1/00006* (2013.01); *A61B 1/00009* (2013.01); *A61B 1/00096* (2013.01); *A61B 1/00193* (2013.01); *A61B 1/012* (2013.01); *A61B 1/042* (2013.01); *A61B 1/045* (2013.01); *A61B 1/0669* (2013.01); *A61B 1/07* (2013.01);
(Continued)

(58) Field of Classification Search
CPC .................................................. A61B 1/00193
USPC .................................................. 600/166, 111
See application file for complete search history.

(56) References Cited

U.S. PATENT DOCUMENTS 4,048,486 A * 9/1977 Kriege ..................... A61B 1/07
362/554
4,633,882 A * 1/1987 Matsuo ................ A61B 1/0052
600/146
(Continued)

FOREIGN PATENT DOCUMENTS

JP     H06-265796 A    9/1994
JP     2002-102163 A   4/2002
(Continued)

OTHER PUBLICATIONS

Office Action dated Dec. 15, 2020, in corresponding Japanese patent Application No. 2017-045354, 8 pages.

*Primary Examiner* — Michael J Carey
*Assistant Examiner* — Minqiao Huang
(74) *Attorney, Agent, or Firm* — Xsensus LLP

(57) ABSTRACT

A medical endoscope system adapted to be inserted into a living body to image an interior of the living body includes: an imaging device that includes a distal end part inserted into the living body to illuminate the living body, and condenses light from the living body to generate two imaging signals having parallaxes; first and second light source units configured to generate first illumination light and second illumination light for illuminating the living body respectively, and supply the first illumination light and the second illumination light to the imaging device; and a display image generation unit configured to generate a display image signal based on the two imaging signals from the imaging device.

10 Claims, 9 Drawing Sheets

(51) Int. Cl.
*A61B 1/00* (2006.01)
*A61B 1/045* (2006.01)
*A61B 1/002* (2006.01)
*A61B 1/04* (2006.01)
*A61B 1/05* (2006.01)
*A61B 1/07* (2006.01)

(52) U.S. Cl.
CPC ....... *A61B 1/00045* (2013.01); *A61B 1/00195* (2013.01); *A61B 1/05* (2013.01)

(56) References Cited

U.S. PATENT DOCUMENTS

| | | | | |
|---|---|---|---|---|
| 4,862,873 A * | 9/1989 | Yajima | ............... | A61B 1/00193 600/111 |
| 4,920,413 A * | 4/1990 | Nakamura | ......... | A61B 1/00039 348/536 |
| 5,441,043 A * | 8/1995 | Wood | ...................... | A61B 1/04 348/75 |
| 5,500,918 A * | 3/1996 | Pileski | ............... | A61B 1/00117 385/117 |
| 6,036,343 A * | 3/2000 | Tomioka | .................. | A61B 1/07 362/268 |
| 6,883,952 B2 * | 4/2005 | Sander | .................. | G02B 21/06 362/231 |
| 8,002,697 B2 * | 8/2011 | Moriyama | .......... | G02B 23/2461 600/113 |
| 8,123,680 B2 * | 2/2012 | Kato | ........................ | A61B 1/07 600/177 |
| 2002/0035310 A1 * | 3/2002 | Akui | ........................ | A61B 1/07 600/111 |
| 2003/0045780 A1 * | 3/2003 | Utsui | ..................... | A61B 1/043 600/182 |
| 2006/0287576 A1 * | 12/2006 | Tsuji | .................. | A61B 1/00105 600/132 |
| 2011/0257483 A1 * | 10/2011 | Mizuyoshi | ......... | G02B 23/2469 600/178 |
| 2011/0257484 A1 * | 10/2011 | Mizuyoshi | ......... | G02B 23/2453 600/178 |
| 2012/0245421 A1 * | 9/2012 | Kitano | ............... | A61B 1/00167 600/180 |
| 2013/0300829 A1 * | 11/2013 | Urasaki | ............. | A61B 1/00009 348/45 |
| 2014/0210945 A1 * | 7/2014 | Morizumi | .......... | A61B 1/00096 348/45 |
| 2015/0045678 A1 * | 2/2015 | Ohzawa | ............... | A61B 5/0084 600/478 |

FOREIGN PATENT DOCUMENTS

WO    WO 2013/031512 A1    3/2013
WO    2016/103411 A1    6/2016

* cited by examiner

MEDICAL ENDOSCOPE SYSTEM PROVIDING ENHANCED ILLUMINATION

CROSS-REFERENCE TO RELATED APPLICATION

The present application claims priority to and incorporates by reference the entire contents of Japanese Patent Application No. 2017-045354 filed in Japan on Mar. 9, 2017.

BACKGROUND

The present disclosure relates to a medical endoscope system.

In the field of medical endoscope systems, a demand for stereoscopic observation has been growing. In the related art, there are known various systems as an endoscope system for stereoscopic vision. For example, WO 2013/031512 discloses an endoscope system for stereoscopic vision including a rigid endoscope that includes optical systems for a left eye and for a right eye, and two imaging units that image an image signal for a left eye and an image signal for a right eye, respectively, based on light condensed by each of the optical systems.

SUMMARY

Comparing a rigid endoscope for stereoscopic vision and a rigid endoscope for plan view both having the same diameter, the rigid endoscope for stereoscopic vision includes two optical systems, so that an aperture of each optical system is smaller than an aperture of an optical system included in the rigid endoscope for plan view. Typically, substantially the same quantity of illumination light is emitted to a living body from distal ends of rigid endoscopes having the same diameter, so that the light quantity taken in by each of the two optical systems of the rigid endoscope for stereoscopic vision is smaller than the light quantity taken in by the optical system of the rigid endoscope for plan view having the same diameter. Thus, in the endoscope system for stereoscopic vision, the quantity of illumination light may be insufficient in some cases.

According to one aspect of the present disclosure, there is provided a medical endoscope system adapted to be inserted into a living body to image an interior of the living body, including: an imaging device that includes a distal end part inserted into the living body to illuminate the living body, and condenses light from the living body to generate two imaging signals having parallaxes; first and second light source units configured to generate first illumination light and second illumination light for illuminating the living body respectively, and supply the first illumination light and the second illumination light to the imaging device; and a display image generation unit configured to generate a display image signal based on the two imaging signals from the imaging device.

DETAILED DESCRIPTION

Figure 1:
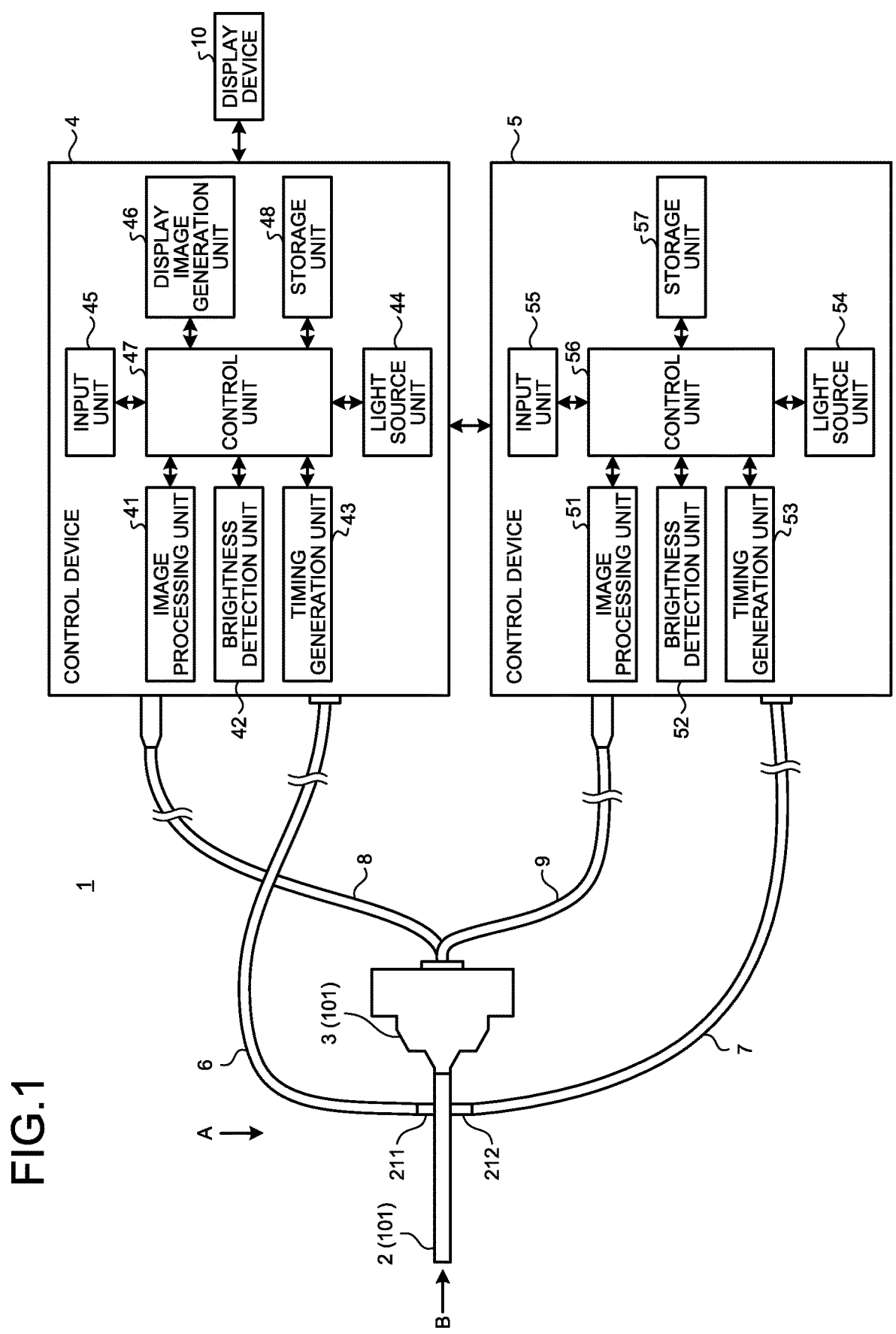
FIG. 1 is a diagram illustrating a schematic configuration of a medical endoscope system according to a first embodiment.

The following describes modes for carrying out the present disclosure (hereinafter, referred to as "embodiments") with reference to the attached drawings. In the drawings, the same portions are denoted by the same reference numerals. The drawings are schematic only, so that dimensions of the same portion or a size ratio between the same portions may be different between different drawings.

First Embodiment

FIG. 1 is a diagram illustrating a schematic configuration of a medical endoscope system according to a first embodiment. A medical endoscope system 1 illustrated in FIG. 1 is a system for stereoscopically observing an interior of a living body. The medical endoscope system 1 includes a rigid endoscope 2 the distal end part of which is inserted into the living body to condense light inside the living body and illuminates the living body, a camera head 3 that images the light from the living body condensed by the rigid endoscope 2 and generates two image signals having parallaxes, a control device (first control device) 4 that controls an operation of the camera head 3 and generates first illumination light to be supplied to the rigid endoscope, a control device (second control device) 5 that controls the operation of the camera head 3 and generates second illumination light to be supplied to the rigid endoscope, a light guide cable (first light guide cable) 6 that connects the rigid endoscope 2 with the control device 4 and transmits the first illumination light, a light guide cable (second light guide cable) 7 that connects the rigid endoscope 2 with the control device 5 and transmits the second illumination light, two transmission cables 8 and 9 that connect the camera head 3 with the respective control devices 4 and 5 and transmit an electric signal and the like, and a display device 10 that is connected to the control device 4 and displays information such as an image. The rigid endoscope 2 and the camera head 3 constitute an imaging device 101.

Figure 2:
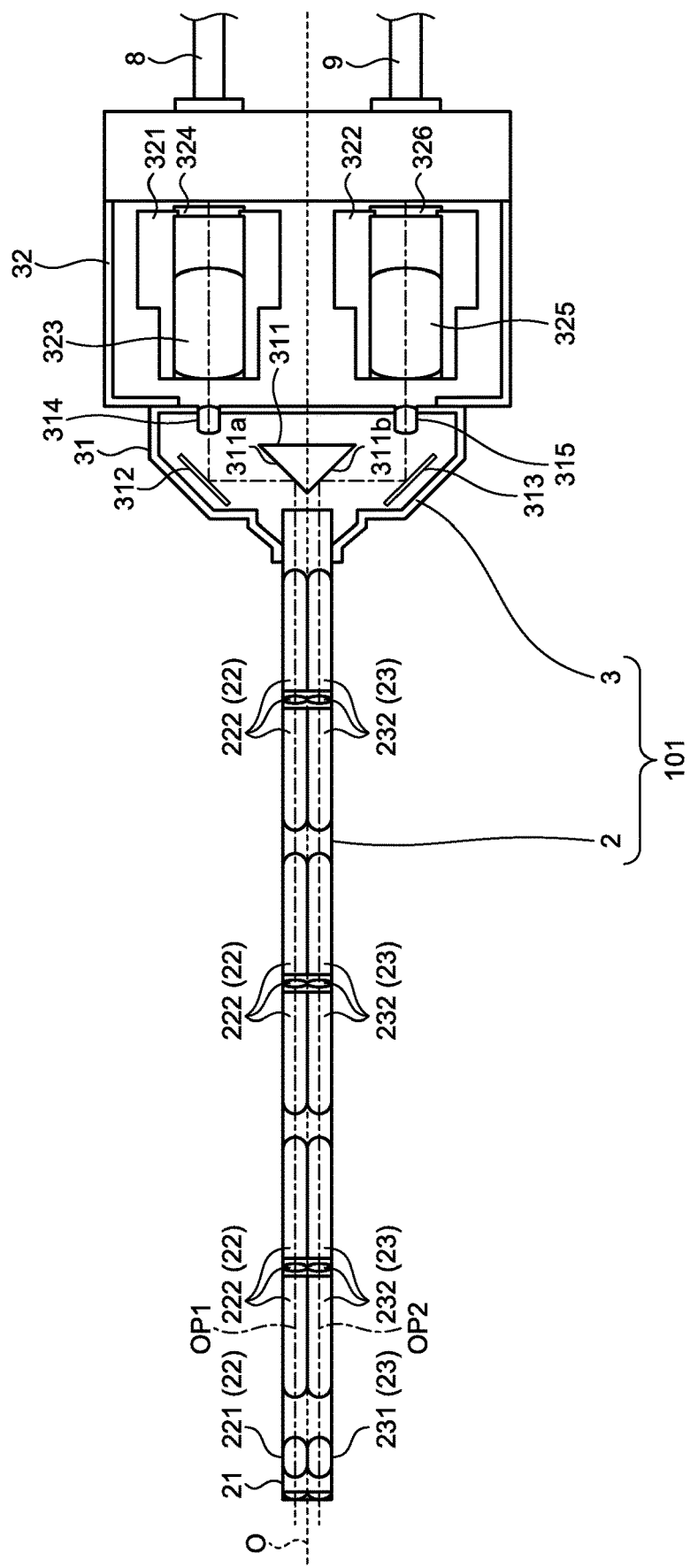
FIG. 2 is a diagram illustrating an internal structure of a rigid endoscope and a camera head included in the medical endoscope system according to the first embodiment.
Figure 3:
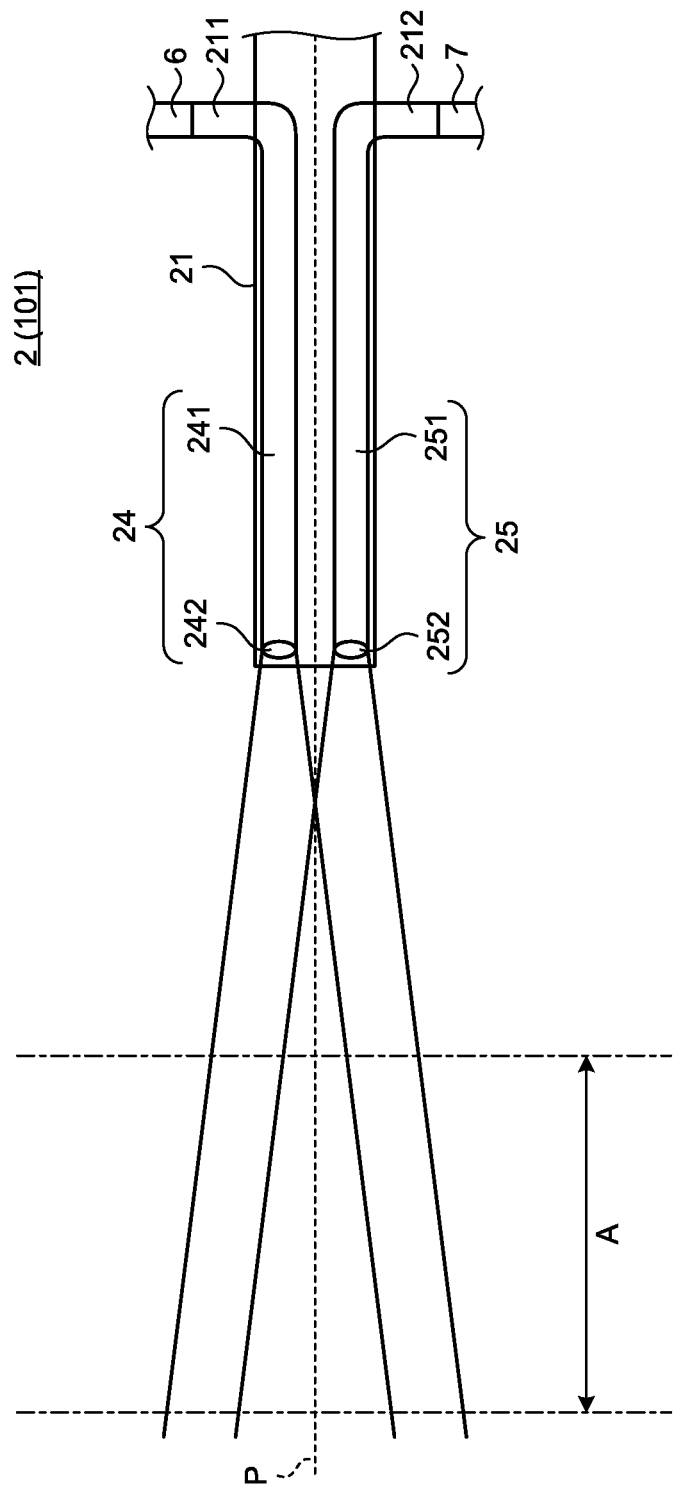
FIG. 3 is a diagram illustrating an internal structure of the rigid endoscope included in the medical endoscope system according to the first embodiment and an irradiation region of illumination light.

FIG. 2 is a diagram illustrating an internal structure of the rigid endoscope 2 and the camera head 3, and illustrating the internal structure of the rigid endoscope 2 and the camera head 3 viewed from the arrow-A direction in FIG. 1. FIG. 3 is a diagram illustrating the internal structure of the rigid endoscope 2, and illustrating the internal structure near a center axis of the rigid endoscope 2 in a state illustrated in FIG. 1. FIG. 2 and FIG. 3 illustrate the internal structure of the rigid endoscope 2 viewed from directions orthogonal to each other. FIG. 3 also schematically illustrates irradiation regions of the first illumination light and the second illumination light.

First, the following describes a configuration of the rigid endoscope 2. The rigid endoscope 2 includes a hard insertion tube 21 having a long and narrow shape, a first condensing optical system 22 and a second condensing optical system 23 arranged in parallel inside the insertion tube 21, and a first illumination optical system 24 and a second illumination optical system 25 that propagate illumination light from respective light sources included in the control devices 4 and 5 and irradiate the living body with the illumination light. The rigid endoscope 2 is connected to the camera head 3 in a removable and unrotatable manner.

On an outer peripheral part of the insertion tube 21, a first mounting unit 211 on which a distal end part of the light guide cable 6 is mounted and a second mounting unit 212 on which a distal end part of the light guide cable 7 is mounted are arranged at positions opposed to each other in a radial direction. The first mounting unit 211 and the second mounting unit 212 are orthogonal to a center axis O of the insertion tube 21, and extend in opposite directions. As illustrated in FIG. 3, the first mounting unit 211 and the second mounting unit 212 are connected to the first illumination optical system 24 and the second illumination optical system 25, respectively, within the insertion tube 21. The first mounting unit 211 and the second mounting unit 212 are also called light guide posts. The first mounting unit 211 and the second mounting unit 212 may be arranged at different positions instead of being arranged at the same position along the center axis direction of the insertion tube 21.

The first condensing optical system 22 includes a first objective optical system 221 and a first relay optical system 222 in this order from a side of the distal end part of the insertion tube 21. The first objective optical system 221 is arranged at the distal end part of the insertion tube 21, and condenses first observation light from an observation part within the living body. The first relay optical system 222 guides the first observation light condensed by the first objective optical system 221 to a base end (a right end part in FIG. 2) of the insertion tube 21. The first observation light is emitted to the camera head 3 from the base end of the insertion tube 21.

Similarly to the first condensing optical system 22, the second condensing optical system 23 includes a second objective optical system 231 and a second relay optical system 232 in this order from the distal end side. Second observation light condensed by the second condensing optical system 23 is emitted to the camera head 3 from the base end of the insertion tube 21. Within the insertion tube 21, the second condensing optical system 23 is separated from the first condensing optical system 22 in a radial direction of the insertion tube 21. An optical axis OP2 of the second condensing optical system 23 is arranged at a position symmetric to an optical axis OP1 of the first condensing optical system 22 with respect to the center axis O of the insertion tube 21.

The first illumination optical system 24 includes a light guide 241 that is connected to the first mounting unit 211 and propagates the first illumination light from the light guide cable 6, and a first illumination lens 242 that emits the first illumination light from the light guide 241 to the outside of the insertion tube 21.

Similarly, the second illumination optical system 25 includes a light guide 251 that is connected to the second mounting unit 212 and propagates the second illumination light from the light guide cable 7, and a second illumination lens 252 that emits the second illumination light from the light guide 251 to the outside of the insertion tube 21. Each of the light guides 241 and 251 is configured by bundling a plurality of optical fibers.

Figure 4:
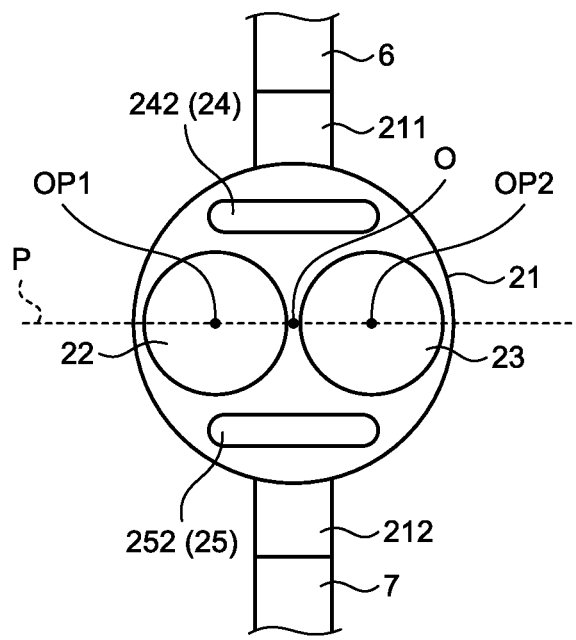
FIG. 4 is a diagram illustrating a configuration of a distal end part of the rigid endoscope included in the medical endoscope system according to the first embodiment.

FIG. 4 is a diagram illustrating a configuration of the distal end part of the rigid endoscope 2, and is a plan view viewed from the arrow-B direction in FIG. 1. As illustrated in FIG. 4, the first illumination lens 242 and the second illumination lens 252 are arranged at symmetric positions with respect to a plane P through which the optical axis OP1 of the first condensing optical system 22 and the optical axis OP2 of the second condensing optical system 23 pass, and the center axis O of the insertion tube 21 passes, at the distal end of the insertion tube 21. Accordingly, the first illumination light emitted from the first illumination lens 242 and the second illumination light emitted from the second illumination lens 252 are emitted to symmetric regions with respect to the plane P as illustrated in FIG. 3. In the first embodiment, light distribution angles of the first illumination lens 242 and the second illumination lens 252 are set so that two pieces of illumination light overlap with each other in a predetermined observation target region A. Accordingly, as compared with a case in which only one light guide is provided as in the related art, the quantity of illumination light emitted to the vicinity of the center of an angle of view of the imaging device 101 may be increased to be substantially twice especially in the observation target region A. The observation target region A is appropriately determined in accordance with conditions such as focal lengths of the first condensing optical system 22 and the second condensing optical system 23, an angle of view when the camera head 3 takes an image, and zoom magnification.

Next, the following describes a configuration of the camera head 3 with reference to FIG. 2. The camera head 3 includes an optical path separation unit 31 that separates an optical path of the first observation light from the first condensing optical system 22 from an optical path of the second observation light from the second condensing optical system 23, and an imaging unit 32 that images the first observation light and the second observation light to generate two image signals.

The optical path separation unit 31 includes a triangular prism 311 that reflects the first observation light and the second observation light to change the optical paths thereof to opposite directions, a pair of mirrors 312 and 313 that reflect the first observation light and the second observation light reflected by the triangular prism 311 to cause the optical paths thereof to be parallel with each other, and a pair of eyepiece optical systems 314 and 315 that emit the first observation light and the second observation light reflected by the respective mirrors 312 and 313 to the imaging unit 32.

The triangular prism 311 has a triangular column shape the bottom face of which is a rectangular equilateral triangle, and a first side surface 311a and a second side surface 311b having the same area and being orthogonal to each other are arranged at an angle of 45 degrees to the optical axis OP1 of the first condensing optical system 22 and the optical axis OP2 of the second condensing optical system 23 in the rigid endoscope 2 mounted to the camera head 3, respectively. The first side surface 311a reflects the first observation light, and bends the optical path thereof by 90 degrees to be upward in FIG. 2. The second side surface 311b reflects the second observation light, and bends the optical path thereof by 90 degrees to be downward in FIG. 2.

The mirror 312 and the mirror 313 are arranged at symmetric positions with respect to the center axis O of the insertion tube 21 of the rigid endoscope 2 connected to the camera head 3. The surface of the mirror 312 forms an angle of 45 degrees to a direction in which the first observation light reflected by the first side surface 311a enters, and reflects the first observation light in a direction parallel with the center axis O. The surface of the mirror 313 forms an angle of 45 degrees to a direction in which the second observation light reflected by the second side surface 311b enters, and reflects the second observation light in a direction parallel with the center axis O.

The eyepiece optical system 314 and the eyepiece optical system 315 are arranged at symmetric positions with respect to the center axis of the insertion tube 21. The first observation light reflected by the mirror 312 passes through the eyepiece optical system 314 and enters the imaging unit 32. The second observation light reflected by the mirror 313 passes through the eyepiece optical system 315 and enters the imaging unit 32.

The imaging unit 32 includes a first imaging unit 321 that images the first observation light to generate an image signal (image signal for a right eye), and a second imaging unit 322 that images the second observation light to generate an image signal (image signal for a left eye).

The first imaging unit 321 includes a first imaging optical system 323 that condenses the first observation light emitted from the eyepiece optical system 314, and a first imaging element 324 that performs photoelectric conversion on the first observation light condensed by the first imaging optical system 323 to generate the image signal for a right eye. The first imaging optical system 323 is constituted of one or a plurality of lenses that are movable along the optical axis, and includes an optical zoom mechanism (not illustrated) for changing an angle of view and a focus mechanism (not illustrated) for changing a focus under control of the control device 4. The first imaging element 324 is constituted of an image sensor such as a charge coupled device (CCD) or a complementary metal oxide semiconductor (CMOS).

The second imaging unit 322 includes a second imaging optical system 325 that condenses the second observation light emitted from the eyepiece optical system 315, and a second imaging element 326 that performs photoelectric conversion on the second observation light condensed by the second imaging optical system 325 to generate the image signal for a left eye. The optical axis of the second imaging optical system 325 is parallel with the optical axis of the first imaging optical system 323. The configurations of the second imaging optical system 325 and the second imaging element 326 are the same as the configurations of the first imaging optical system 323 and the first imaging element 324, respectively. The optical zoom mechanism and the focus mechanism included in the second imaging optical system 325 are driven under control of the control device 5.

Next, the following describes the configurations of the control devices 4 and 5 with reference to FIG. 1. In the first embodiment, the control device 4 and the control device 5 serve as a master and a slave, respectively, and perform control in synchronization with each other. The control device 4 serving as a master receives the image signal for a left eye generated by the second imaging unit 322 from the control device 5 serving as a slave, and generates a display image signal (three-dimensional image signal) together with the image signal for a right eye received from the first imaging unit 321 to be output to the display device 10.

The control device 4 includes an image processing unit 41 that performs predetermined image processing on the image signal generated by the first imaging unit 321, a brightness detection unit 42 that detects brightness of the image signal generated by the first imaging unit 321, a timing generation unit 43 that generates a signal for synchronizing the camera head 3 and the control device 5, a light source unit (first light source unit) 44 that generates the first illumination light to be supplied to the light guide cable 6, an input unit 45 that receives inputs of various operation signals, a display image generation unit 46 that generates a display image signal to be displayed on the display device 10, a control unit 47 that controls an operation of the medical endoscope system 1 including the control device 4, and a storage unit 48 that stores various pieces of information. The control device 4 is connected to the control device 5 via the transmission cable, receives various pieces of information including the image signal from the control device 5, and transmits various control signals and the like to the control device 5. Communication between the control device 4 and the control device 5 may be performed in a wireless manner.

The image processing unit 41 performs image processing such as synchronization processing, white balance (WB) adjustment processing, gain adjustment processing, gamma correction processing, digital/analog (D/A) conversion processing, and format conversion processing on the image signal to be output to the brightness detection unit 42 and the display image generation unit 46.

The brightness detection unit 42 detects brightness of an image in the image signal from the image processing unit 41. The brightness detection unit 42 measures, for example, a signal value (luminance value) of each pixel, calculates an average value thereof as a signal level, and outputs a calculation result to the control unit 47 as brightness information. The brightness detection unit 42 may calculate, as the signal level, any of a maximum value, a minimum value, a mode, and the like instead of the average value of the signal values of the pixels.

The timing generation unit 43 generates a vertical synchronizing signal representing start timing of a clock signal and an image signal for each frame as a standard of an operation of each constituent part of the camera head 3 and the control device 5, and outputs the vertical synchronizing signal to the camera head 3 and the control device 5.

The light source unit 44 includes a light source constituted of a light emitting diode (LED), a halogen lamp, or the like, a light source driver that drives the light source under control of the control unit 47, and an emission optical system that condenses light generated by the light source to be emitted to the light guide.

The input unit 45 is a user interface that receives inputs of various operation signals related to the medical endoscope system 1 including the control device 4.

The display image generation unit 46 generates a three-dimensional image signal corresponding to a display system of the display device 10 as a display image signal using the image signal for a right eye generated by the first imaging unit 321 and the image signal for a left eye that is generated by the second imaging unit 322 and received from the control device 5.

The control unit 47 controls the medical endoscope system 1 in a centralized manner by controlling operations of the image processing unit 41, the light source unit 44, and the display image generation unit 46, controlling an operation of the camera head 3, and performing control to be operated in cooperation with the control device 5. The control unit 47 adjusts a light quantity ratio between the light source unit 44 and the light source unit 54 included in the control device 5 using the brightness information input from the brightness detection unit 42 and brightness information transmitted from the control device 5, and transmits a light source control signal to each of the light source units 44 and 54.

The storage unit 48 stores various computer programs for operating the control device 4. The computer programs include a computer program to be used when the control device 4 serving as a master controls the medical endoscope system 1 in a centralized manner. The storage unit 48 is constituted of a volatile memory such as a random access memory (RAM) and a nonvolatile memory such as a read only memory (ROM).

In the control device 4 having the functional configuration described above, the image processing unit 41, the brightness detection unit 42, the timing generation unit 43, the display image generation unit 46, and the control unit 47 are constituted of a general-purpose processor such as a central processing unit (CPU), a dedicated integrated circuit that executes a specific function such as a field programmable gate array (FPGA), and the like.

The control device 5 includes an image processing unit 51, a brightness detection unit 52, a timing generation unit 53, a light source unit (second light source unit) 54, an input unit 55, a control unit 56, and a storage unit 57. Each of the components has the same functional configuration as that of the corresponding component of the control device 4 described above. However, the control unit 56 performs control for causing the control device 5 to operate as a slave. The storage unit 57 stores a computer program for causing the control device 5 to operate as a slave.

Each of the light guide cables 6 and 7 is configured by bundling a plurality of optical fibers. One end of the light guide cable 6 is connected to the control device 4, and the other end thereof is mounted to the first mounting unit 211 of the rigid endoscope 2 to guide the first illumination light generated by the control device 4 to the light guide 241. One end of the light guide cable 7 is connected to the control device 5, and the other end thereof is mounted to the second mounting unit 212 of the rigid endoscope 2 to guide the second illumination light generated by the control device 5 to the light guide 251.

Communication between the camera head 3 and the control device 4 and communication between the camera head 3 and the control device 5 are performed via the transmission cables 8 and 9, respectively. Each of the transmission cables 8 and 9 is a metal cable that transmits an electric signal. Each of the transmission cables 8 and 9 may be a fiber cable that transmits an optical signal. In this case, an electric/optic (E/O) conversion function may be provided to the camera head 3, and an optic/electric (O/E) conversion function may be provided to each of the control devices 4 and 5. Each of the transmission cables 8 and 9 may be configured by combining a metal cable and a fiber cable, only an image signal may be transmitted with an optical signal, and other signals may be transmitted with an electric signal. Communication between the camera head 3 and each of the control devices 4 and 5 may be performed in a wireless manner.

The display device 10 is, for example, a three-dimensional display of an integral imaging type or a multi-eye type using liquid crystals, organic electro luminescence (EL), and the like, and displays a three-dimensional image based on the three-dimensional image signal generated by the control device 4.

According to the first embodiment described above, the illumination light quantity is increased because the living body is illuminated with two pieces of illumination light, so that the illumination light quantity for stereoscopic vision may be secured. As a result, an image to be taken is brightened, and noise in a dark part that may be caused through image processing may be reduced, and a clear three-dimensional image may be displayed.

According to the first embodiment, by using two light source integrated control devices 4 and 5, illumination light having a light quantity that is about twice that in a case of using only one light source device in the related art may be emitted to the living body. Accordingly, the light quantity of the illumination light for stereoscopic vision may be supplied with a simple configuration.

In the first embodiment, described is a case in which the control device 4 and the control device 5 serve as a master and a slave, respectively. Alternatively, the control device 4 and the control device 5 may have an equal relation. In this case, the configuration may be such that the control device 4 outputs the image signal for a right eye to the display device 10, the control device 5 outputs the image signal for a left eye to the display device 10, and the display device 10 that has received two image signals as a pair generates the display image signal. When the control device 4 and the control device 5 are assumed to have an equal relation, an image generation device may be provided, the image generation device being connected to the control devices 4 and 5 and the display device 10 and generating a three-dimensional display image signal to be output to the display device 10 based on the image signal from the control devices 4 and 5.

Modification

Figure 5:
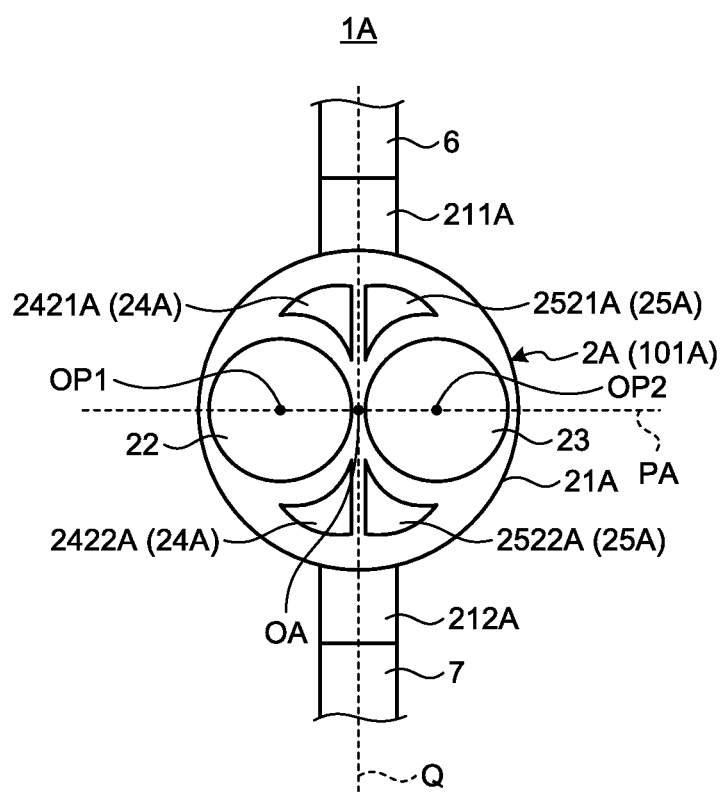
FIG. 5 is a diagram illustrating a configuration of a distal end part of a rigid endoscope included in a medical endoscope system according to a modification of the first embodiment.

FIG. 5 is a diagram illustrating a configuration of a distal end part of the rigid endoscope included in the medical endoscope system according to a modification of the first embodiment. In a medical endoscope system 1A illustrated in FIG. 5, a first illumination optical system 24A connected to a first mounting unit 211A of a rigid endoscope 2A is divided into two pieces inside an insertion tube 21A. At a distal end part of the insertion tube 21A, as illustrated in FIG. 5, two first divided illumination lenses 2421A and 2422A are arranged. The first divided illumination lens 2421A and the first divided illumination lens 2422A are arranged at symmetric positions with respect to a plane PA through which a center axis OA of the insertion tube 21A, the optical axis OP1 of the first condensing optical system 22, and the optical axis OP2 of the second condensing optical system 23 pass.

Similarly, a second illumination optical system 25A connected to a second mounting unit 212A is also divided into two pieces inside the insertion tube 21. At the distal end part of the insertion tube 21A, as illustrated in FIG. 5, two second divided illumination lenses 2521A and 2522A are arranged. The second divided illumination lens 2521A and the second divided illumination lens 2522A are also arranged at symmetric positions with respect to the plane PA. The second divided illumination lenses 2521A and 2522A are arranged at positions symmetric to the respective first divided illumination lenses 2421A and 2422A with respect to a plane Q that is orthogonal to the plane PA and passes through the center axis OA of the insertion tube 21A.

The rigid endoscope 2A having the configuration described above configures an imaging device 101A together with the camera head 3.

According to the modification of the first embodiment described above, the same effect as that of the first embodiment may be obtained. According to the present modification, the first illumination light and the second illumination light are emitted to symmetric regions with respect to the plane PA described above, so that the light quantity of the illumination light may be adjusted along a direction different by 90 degrees from that in the first embodiment. Thus, depending on a situation of the living body as an observation target, the rigid endoscope 2 described in the first embodiment and the rigid endoscope 2A described in the present modification may be appropriately used. Accordingly, a clearer image corresponding to the situation of the living body may be acquired.

Second Embodiment

A medical endoscope system according to a second embodiment has the same configuration as that of the medical endoscope system according to the first embodiment except the configuration of the rigid endoscope. In the following description, components other than the rigid endoscope in the medical endoscope system according to the second embodiment are denoted by the same reference numerals as those of the components of the medical endoscope system according to the first embodiment.

Figure 6:
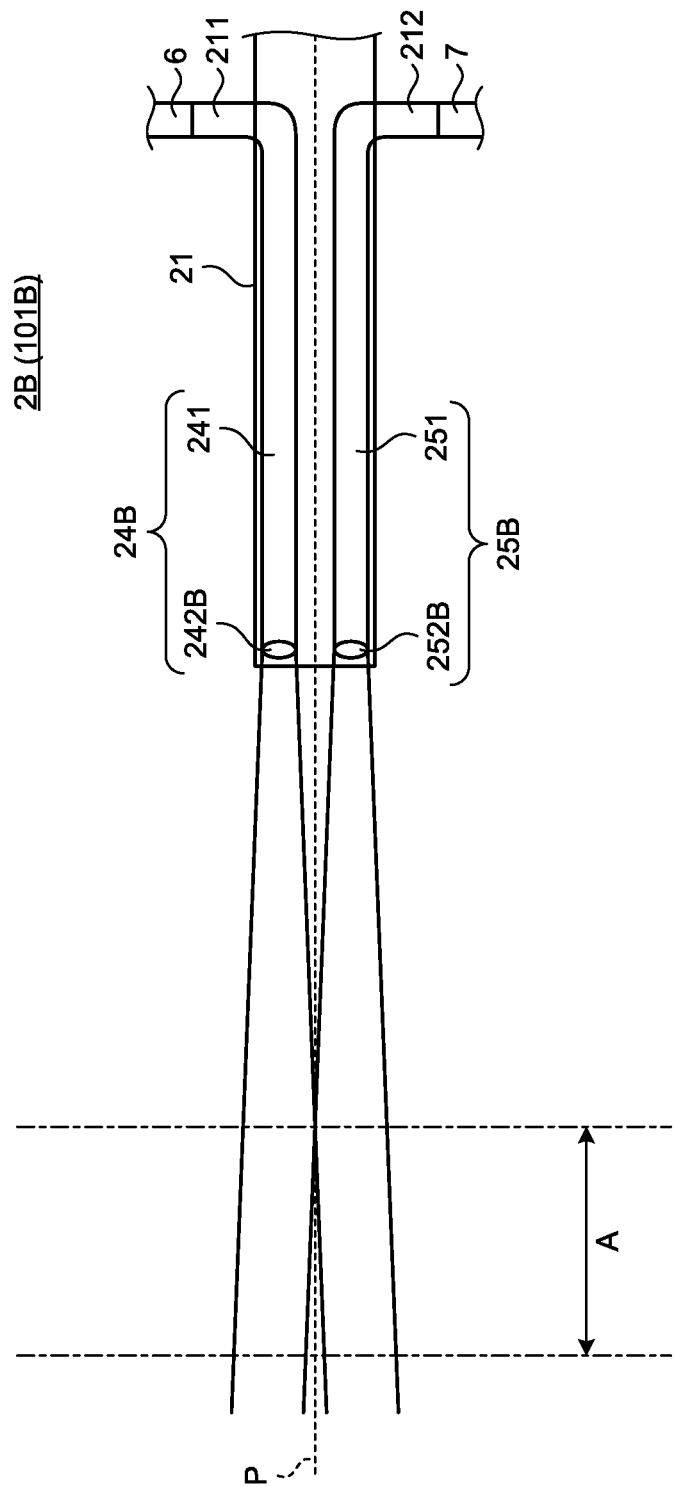
FIG. 6 is a diagram illustrating an internal structure of a rigid endoscope included in a medical endoscope system according to a second embodiment and an irradiation region of illumination light.

FIG. 6 is a diagram schematically illustrating a configuration of a principal part of the distal end part of the rigid endoscope included in the medical endoscope system according to the second embodiment, and an irradiation region of the illumination light. A rigid endoscope 2B illustrated in FIG. 6 includes a first illumination optical system 24B and a second illumination optical system 25B. The first illumination optical system 24B includes the light guide 241 and a first illumination lens 242B that is arranged on a distal end side of the light guide 241 and narrows (reduces) a light distribution angle of the first illumination light to emit substantially the whole first illumination light to one side (an upper side of the plane P in FIG. 6) with respect to the plane P passing through the optical axis OP1 of the first condensing optical system 22, the optical axis OP2 of the second condensing optical system 23, and the center axis O of the insertion tube 21. Similarly, the second illumination optical system 25B includes the light guide 251 and a second illumination lens 252B that is arranged on a distal end side of the light guide 251 and narrows the light distribution angle of the second illumination light to emit substantially the whole second illumination light to the other side (a lower side of the plane P in FIG. 6) with respect to the plane P. Each of the first illumination lens 242B and the second illumination lens 252B is, for example, constituted of a light distribution angle conversion lens. In the case illustrated in FIG. 6, the first illumination light and the second illumination light are emitted to regions being symmetric to each other with respect to the plane P and not overlapping with each other until within the predetermined observation target region A.

The light quantity per unit area of the first illumination light and the second illumination light according to the second embodiment is large as the light distribution angle is narrow. Thus, in the second embodiment, as compared with a case in which only one light guide is provided as in the related art, the light quantity of the illumination light emitted to the vicinity of the center of the angle of view of an imaging device 101B may be increased especially in the observation target region A.

According to the second embodiment described above, emitted are the first illumination light and the second illumination light having narrow light distribution angles and irradiation regions not much overlapping with each other, so that the light quantity per unit area of each piece of illumination light may be increased. Thus, according to the second embodiment, similarly to the first embodiment, the illumination light quantity for stereoscopic vision may be secured and a clear three-dimensional image may be displayed with less noise in a dark part.

In the second embodiment, light quantity control of the first illumination light by the control device 4 and light quantity control of the second illumination light by the control device 5 may be independently performed by utilizing the fact that the irradiation regions of the first illumination light and the second illumination light do not much overlap with each other. Specifically, the control unit 47 may control the light source unit 44 based on a detection result of the brightness detection unit 42 of the control device 4, and the control unit 56 may control the light source unit 54 based on a detection result of the brightness detection unit 52 of the control device 5.

For example, when treatment is provided utilizing an electric scalpel within a living body corresponding to a lower half region of a screen, the lower half region of the screen may be projected to be bright but an upper half region of the screen may be projected to be dark. In this case, the control device 4 may perform control for increasing the light quantity of the first illumination light generated by the light source unit 44, and the control device 5 may perform control for maintaining or reducing the light quantity of the second illumination light generated by the light source unit 54. Accordingly, a clear display image having high visibility of the entire screen may be generated.

Instead of automatic adjustment of brightness performed by the control devices 4 and 5, the brightness of the first illumination light and the second illumination light may be adjusted when a user makes an input through the input unit 45 of the control device 4 and the input unit 55 of the control device 5. Alternatively, the brightness of the first illumination light and the second illumination light may be adjusted via an input unit (not illustrated) arranged in the camera head 3.

Third Embodiment

Figure 7:
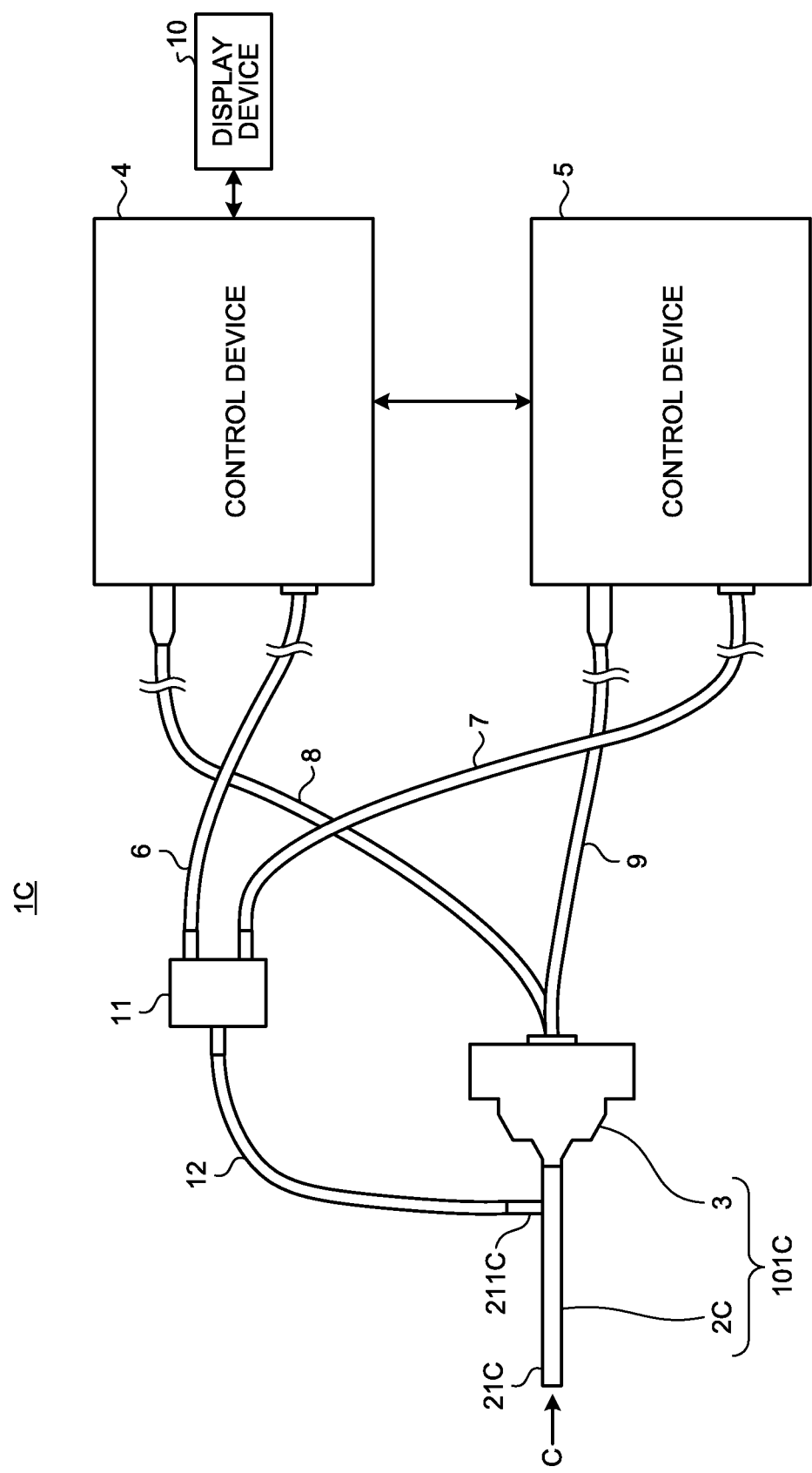
FIG. 7 is a diagram illustrating a schematic configuration of a medical endoscope system according to a third embodiment.

The medical endoscope system according to a third embodiment is different from that in the first embodiment in the configuration of the rigid endoscope and a configuration of propagating the first illumination light and the second illumination light from the control device to the rigid endoscope. FIG. 7 is a diagram illustrating a schematic configuration of the medical endoscope system according to the third embodiment. In the following description, the same components as those in the first embodiment are denoted by the same reference numerals as in the first embodiment.

A medical endoscope system 1C illustrated in FIG. 7 includes a rigid endoscope 2C including an insertion tube 21C on which one mounting unit 211C is arranged, the camera head 3, the two control devices 4 and 5, the light guide cables 6 and 7, the two transmission cables 8 and 9, the display device 10, an illumination light synthesizing unit 11 that synthesizes the first illumination light and the second illumination light propagated through the respective light guide cables 6 and 7, and a light guide cable (third light guide cable) 12 that connects the illumination light synthesizing unit 11 with the mounting unit 211C and guides synthesized illumination light synthesized by the illumination light synthesizing unit 11. The rigid endoscope 2C and the camera head 3 constitute an imaging device 101C.

Figure 8:
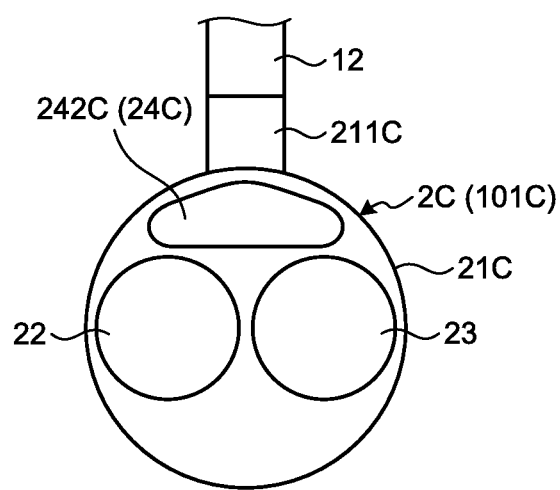
FIG. 8 is a diagram illustrating a configuration of a distal end part of an insertion tube of a rigid endoscope included in the medical endoscope system according to the third embodiment.

FIG. 8 is a diagram illustrating a configuration of a distal end part of the insertion tube 21C included in the rigid endoscope 2C, and is a plan view viewed from the arrow-C direction in FIG. 7. In the third embodiment, the mounting unit 211C is connected to one illumination optical system 24C arranged inside the insertion tube 21C. The illumination optical system 24C includes a light guide (not illustrated) that propagates the synthesized illumination light from the light guide cable 12, and an illumination lens 242C that is arranged at a distal end of the light guide and emits the synthesized illumination light to the outside. By dividing the light guide into two pieces within the insertion tube 21C, the configuration of the distal end may be caused to be the same as that of the insertion tube 21 described in the first embodiment (refer to FIG. 4).

The illumination light synthesizing unit 11 includes an optical system for synthesizing the first illumination light and the second illumination light propagated through the respective light guide cables 6 and 7. The optical system is implemented by appropriately combining a mirror and a triangular prism, for example.

According to the third embodiment described above, the synthesized illumination light obtained by synthesizing the first illumination light and the second illumination light is emitted, so that a larger quantity of illumination light may be emitted as compared with a case of emitting illumination light from one light source. Thus, according to the third embodiment, similarly to the first embodiment, the illumination light quantity for stereoscopic vision may be secured and a clear three-dimensional image may be displayed with less noise in a dark part.

According to the third embodiment, one light guide cable 12 for propagating the synthesized illumination light synthesized by the illumination light synthesizing unit 11 may be mounted to one mounting unit 211C of the insertion tube 21C, so that the rigid endoscope 2C has a simple configuration.

In the third embodiment, the configuration may be such that the illumination light synthesizing unit 11 bundles two light guide cables to be one light guide cable (third light guide cable) to be connected to one mounting unit arranged on the rigid endoscope. The diameter of one bundled light guide cable and the diameter of the mounting unit are about twice the diameter of the light guide cable 12 and the diameter of the mounting unit 211C, respectively. Obviously, the same effect as that in the third embodiment may be obtained with such a configuration.

Fourth Embodiment

Figure 9:
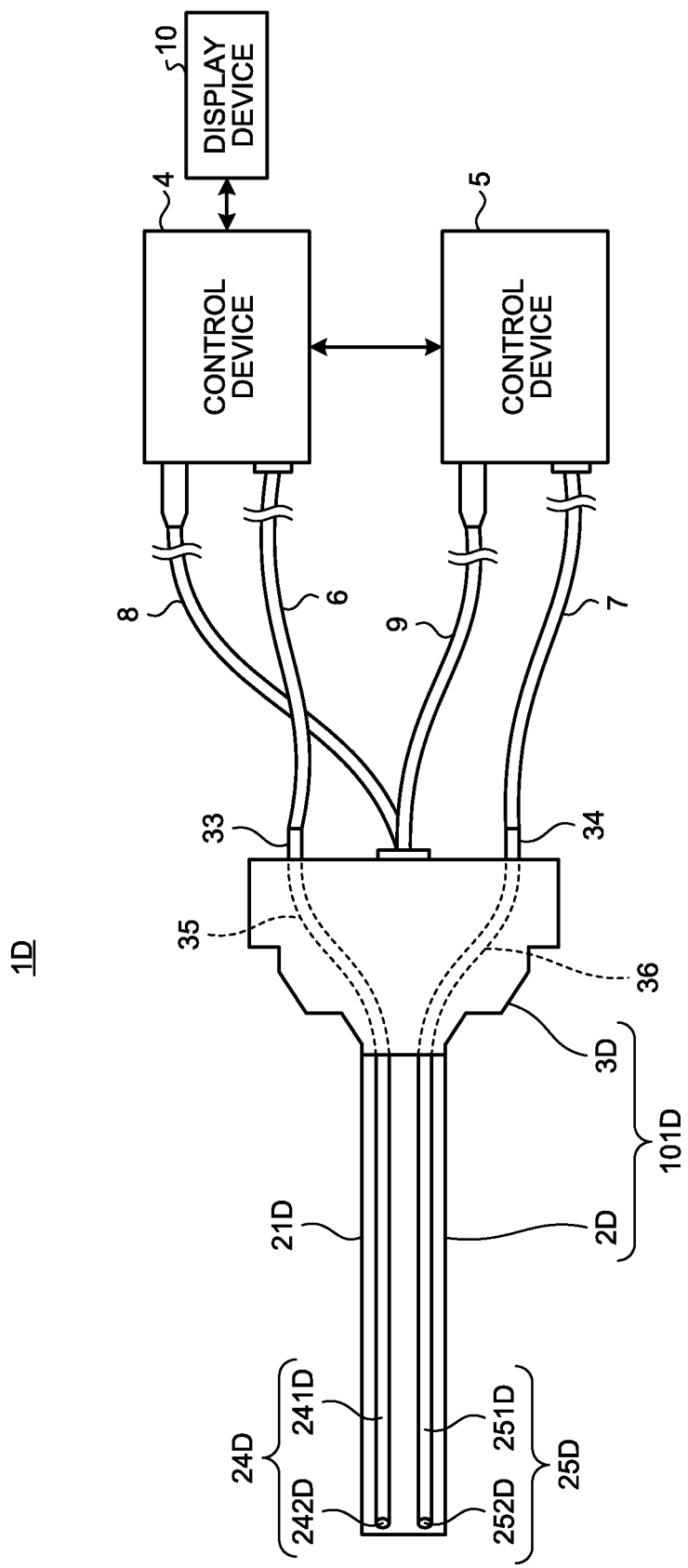
FIG. 9 is a diagram illustrating a configuration of a medical endoscope system according to a fourth embodiment.

FIG. 9 is a diagram illustrating a configuration of the medical endoscope system according to a fourth embodiment. In the following description, the same components as the components of the medical endoscope system according to the first embodiment are denoted by the same reference numerals as in the first embodiment.

A medical endoscope system 1D illustrated in FIG. 9 includes a rigid endoscope 2D, a camera head 3D, the two control devices 4 and 5, the two light guide cables 6 and 7, the two transmission cables 8 and 9, and the display device 10. The rigid endoscope 2D and the camera head 3D constitute an imaging device 101D.

The rigid endoscope 2D includes a first illumination optical system 24D and a second illumination optical system 25D. The first illumination optical system 24D includes a light guide 241D and a first illumination lens 242D. Similarly, the second illumination optical system 25D includes a light guide 251D and a second illumination lens 252D. The rigid endoscope 2D is different from those in the first to the third embodiments described above in that the mounting unit for the light guide cable is not arranged on an outer peripheral part of an insertion tube 21D. The configurations of the first condensing optical system and the second condensing optical system included in the rigid endoscope 2D are the same as the configurations of the first condensing optical system 22 and the second condensing optical system 23 included in the rigid endoscope 2 described in the first embodiment, respectively.

The camera head 3D includes a first mounting unit 33 and a second mounting unit 34 to which respective distal end parts of the light guide cables 6 and 7 are mounted, and light guides 35 and 36 connected to the respective first mounting unit 33 and the second mounting unit 34. The light guides 35 and 36 are connected to the respective light guides 241D and 251D arranged inside the insertion tube 21D of the rigid endoscope 2D mounted to the camera head 3D. In FIG. 9, the light guide cables 6 and 7 are formed on a base end side of the camera head 3D, but forming positions thereof are not limited thereto. For example, the light guide cables 6 and 7 may be formed on an upper end side and a lower end side in FIG. 9, respectively.

The configuration of the medical endoscope system 1D except the above configuration is the same as the configuration of the medical endoscope system 1 described in the first embodiment.

According to the fourth embodiment described above, similarly to the first embodiment, the illumination light quantity for stereoscopic vision may be secured and a clear three-dimensional image may be displayed with less noise in a dark part.

According to the fourth embodiment, the first mounting unit 33 and the second mounting unit 34 are formed on the camera head 3D, so that the light guide cables 6 and 7 are not required to be routed to the rigid endoscope 2D. Accordingly, the rigid endoscope 2D having a simple external appearance configuration may be applied, and a space around the rigid endoscope 2D may be effectively utilized.

Fifth Embodiment

Figure 10:
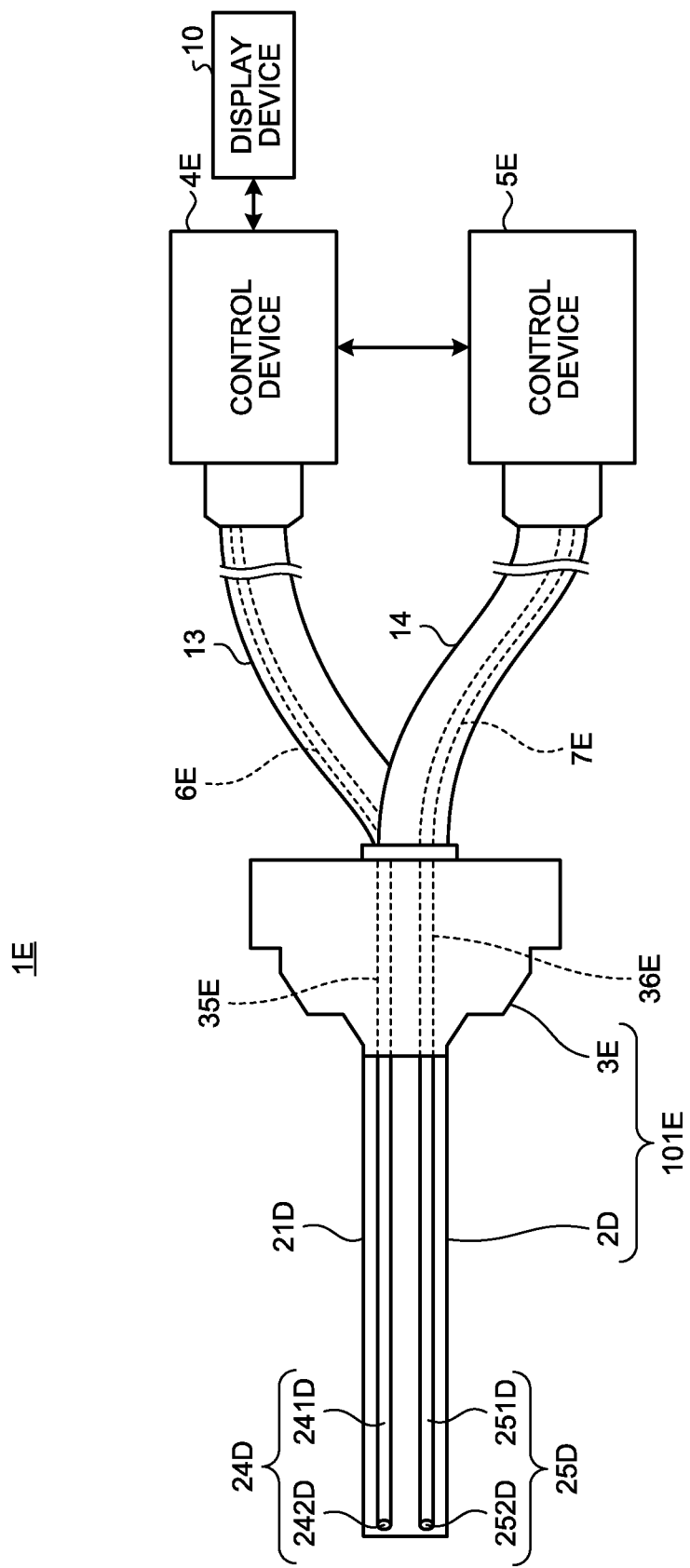
FIG. 10 is a diagram illustrating a configuration of a medical endoscope system according to a fifth embodiment.

FIG. 10 is a diagram illustrating a configuration of the medical endoscope system according to a fifth embodiment. In the following description, the same components as the components of the medical endoscope system according to the first embodiment are denoted by the same reference numerals as in the first embodiment.

A medical endoscope system 1E illustrated in FIG. 10 includes the rigid endoscope 2D described in the fourth embodiment, a camera head 3E, a control device (first control device) 4E, a control device (second control device) 5E, two universal codes 13 and 14 that connect the respective control devices 4E and 5E to the camera head 3E, and the display device 10. The rigid endoscope 2D and the camera head 3E constitute an imaging device 101E.

The universal code 13 is obtained by integrating a light guide cable 6E that propagates the first illumination light generated by the control device 4E and a transmission cable (not illustrated) that transmits an electric signal between the control device 4E and the camera head 3E. Similarly, the universal code 14 is obtained by integrating a light guide cable 7E that propagates the second illumination light generated by the control device 5E and a transmission cable that transmits an electric signal between the control device 5E and the camera head 3E.

The camera head 3E includes a light guide 35E that is connected to the light guide cable 6E in the universal code 13 and propagates the first illumination light, and a light guide 36E that is connected to the light guide cable 7E in the universal code 14 and propagates the second illumination light. The light guides 35E and 36E are respectively connected to the light guides 241D and 251D within the insertion tube 21D of the rigid endoscope 2D mounted to the camera head 3E.

The control devices 4E and 5E have the same configuration as that of the control devices 4 and 5 described in the first embodiment except a configuration of a connection part for connecting each of the universal codes 13 and 14.

According to the fifth embodiment described above, similarly to the first embodiment, the illumination light quantity for stereoscopic vision may be secured and a clear three-dimensional image may be displayed with less noise in a dark part.

According to the fifth embodiment, the universal codes 13 and 14 are configured to be connected to the camera head 3E, so that the light guide cables are not required to be routed to the rigid endoscope 2D. Accordingly, similarly to the fourth embodiment, the rigid endoscope 2D having a simple external appearance configuration may be applied, and a space around the rigid endoscope 2D may be effectively utilized.

Other Embodiments

The modes for carrying out the disclosure have been described above, but the present disclosure is not limited to the first to the fifth embodiments described above. For example, the control device and the light source device may be separately formed. The configuration may include two light source devices and one control device to which the camera head for stereoscopic vision described above may be connected, or may individually include two control devices and two light source devices.

In the first to the fifth embodiments described above, exemplified is the imaging device having a configuration in which the rigid endoscope and the camera head are separately formed, and the rigid endoscope is connected to the camera head in a removable and unrotatable manner. Alternatively, an imaging device in which the rigid endoscope and the camera head are integrally formed may be applied.

According to the present disclosure, the quantity of illumination light for stereoscopic vision may be secured.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:
1. A medical endoscope system adapted to be inserted into a living body to image an interior of the living body, the medical endoscope system comprising:
    a camera that includes a distal end part inserted into the living body to illuminate the living body, and condenses light from the living body to generate two imaging signals having parallaxes;
    first and second light sources configured to generate first illumination light and second illumination light for illuminating the living body respectively, and supply the first illumination light and the second illumination light to the camera;
    first circuitry configured to control the first light source and the camera;
    second circuitry configured to communicate with the first circuitry and to control the second light source and the camera;
    first and second light guide cables configured to connect each of the first and the second light sources to the camera, and propagate the first illumination light and the second illumination light to the camera, wherein
    the camera includes;
        first and second illumination optics configured to propagate the first illumination light and the second illumination light to be emitted to outside; and
        a rigid endoscope configured to be inserted into the living body to condense light from the living body, wherein the rigid endoscope includes;
        the first and the second illumination optics;
        an insertion tube that houses the first and the second illumination optics
        the first and the second illumination optics respectively include first and second illumination lenses arranged at distal end parts of the insertion tube, and
        the first and second illumination optics narrow light distribution angles of the first illumination light and the second illumination light to be emitted; and
    a display configured to generate a display image signal based on the two imaging signals from the camera.
2. The medical endoscope system according to claim 1, wherein
the first and the second circuitries are configured to perform at least part of control in synchronization with each other.
3. The medical endoscope system according to claim 2, wherein
the camera includes:
    first and second mounts to which respective ends of e first and the second light guide cables are mounted; and
    the first and second illumination optics are configured to be connected to the respective first and second mounts.
4. The medical endoscope system according to claim 3, wherein
the rigid endoscope includes:
    first and second condensing optics configured to condense light from the living body.
5. The medical endoscope system according to claim 3, wherein
the camera includes:
    a camera head in which the first and the second mounts are arranged,
    the camera head being configured to generate the two imaging signals using
    the light condensed by the rigid endoscope, and
the rigid endoscope includes:
    first and second condensing optics configured to condense light from the living body.
6. The medical endoscope system according to claim 4, wherein the first and the second condensing optics respectively
include first and second objective optics arranged at
symmetric positions with respect to a center axis of the
insertion tube at distal end parts of the insertion tube,
and the first and second illumination lenses are arranged at
symmetric positions with respect to the center axis of
the insertion tube at distal end parts of the insertion
tube.

7. The medical endoscope system according to claim 1, wherein the first circuitry is configured to control a quantity of light output by the first light source and the second circuitry is configured to control a quantity of light output by the second light source, independent from the control of the quantity of first light source.

8. The medical endoscope system according to claim 1, comprising:

an illumination light synthesizing optics configured to be connected to the first and the second light guide cables, and synthesize the first illumination light and the second illumination light; and a third light guide cable configured to connect the illumination light synthesizing optics to the camera, and propagate synthesized illumination light synthesized by the illumination light synthesizing optics to the camera.

9. A medical endoscope system adapted to be inserted into a living body to image an interior of the living body, the medical endoscope system comprising:

a camera that includes a distal end part inserted into the living body to illuminate the living body, and condenses light from the living body to generate two imaging signals having parallaxes;

first and second light sources configured to generate first illumination light and second illumination light for illuminating the living body respectively, and supply the first illumination light and the second illumination light to the camera;

first circuitry configured to control the first light source and the camera;

second circuitry configured to communicate with the first circuitry and to control the second light source and the camera, wherein the first and the second circuitries are configured to perform al least part of control in synchronization with each other;

first and second light guide cables configured to connect each of the first and the second light sources to the camera, and propagate the first illumination light and the second illumination light to the camera, wherein the camera includes:

first and second mounts to which respective ends of the first and the second light guide cables are mounted;

first and second illumination optics configured to be connected to the respective first and second mounts, and to propagate the first illumination light and the second illumination light to be emitted to outside; and a rigid endoscope configured to be inserted into the living body to condense light from the living body, wherein the rigid endoscope includes:

the first and the second illumination optics;

first and second condensing optics configured to condense light from the living body; and an insertion tube that houses the first and the second illumination optics and the first and the second condensing optics; and includes the first and the second mounts, wherein the first and the second condensing optics respectively
include first and second objective optics arranged at
symmetric positions with respect to a center axis of the
insertion tube at distal end parts of the insertion tube, the first and the second illumination optics respectively
include first and second illumination lenses arranged at
symmetric positions with respect to the center axis of
the insertion tube at distal end parts of the insertion
tube, and the first and second illumination optics narrow light distribution angles of the first illumination light and the second illumination light to be emitted; and a display configured to generate a display image signal based on the two imaging signals from the camera.

10. A medical endoscope system adapted to be inserted into a living body to image an interior of the living body, the medical endoscope system comprising:

a camera that includes a distal end part inserted into the living body to illuminate the living body, and condenses light from the living body to generate two imaging signals having parallaxes;

first and second light sources configured to generate first illumination light and second illumination light for illuminating the living body respectively, and supply the first illumination light and the second illumination light to the camera;

first circuitry configured to control the first light source and the camera;

second circuitry configured to communicate with the first circuitry and to control the second light source and the camera, wherein the first and the second circuitries are configured to perform at least part of control in synchronization with each other;

first and second light guide cables configured to connect each of the first and the second light sources to the camera; and propagate the first illumination light and the second illumination light to the camera, wherein the camera includes:

first and second mounts to which respective ends of the first and the second light guide cables are mounted;

first and second illumination optics configured to be connected to the respective first and second mounts, and to propagate the first illumination light and the second illumination light to be emitted to outside; and a rigid endoscope configured to be inserted into the living body to condense light from the living body, wherein the rigid endoscope includes:

the first and the second illumination optics;

first and second condensing optics configured to condense light from the living body; and an insertion tube that houses the first and the second illumination optics and the first and the second condensing optics, and includes the first and the second mounts, wherein the first and the second condensing optics respectively
include first and second objective optics arranged at
symmetric positions with respect to a center axis of the
insertion tube at distal end parts of the insertion tube, the first and the second illumination optics respectively
include first and second illumination lenses arranged at
symmetric positions with respect to the center axis of
the insertion tube at distal end parts of the insertion
tube, the first circuitry is configured to control a quantity of light output by the first light source, and the second circuitry is configured to control a quantity of light output by the second light source, independent from the control of the quantity of the first light source, and a display configured to generate a display image signal based on the two imaging signals from the camera.

* * * * *